United States Patent
Brucker

(10) Patent No.: US 10,914,717 B2
(45) Date of Patent: Feb. 9, 2021

(54) METHOD AND APPARATUS FOR PARTIAL PRESSURE DETECTION

(71) Applicant: MKS Instruments, Inc., Andover, MA (US)

(72) Inventor: Gerardo A. Brucker, Longmont, CO (US)

(73) Assignee: MKS Instruments, Inc., Andover, MA (US)

( * ) Notice: Subject to any disclaimer, the term of this patent is extended or adjusted under 35 U.S.C. 154(b) by 240 days.

(21) Appl. No.: 15/975,473

(22) Filed: May 9, 2018

(65) Prior Publication Data

US 2019/0346328 A1    Nov. 14, 2019

(51) Int. Cl.
| | |
|---|---|
| G01N 33/00 | (2006.01) |
| G01L 21/12 | (2006.01) |
| F26B 25/22 | (2006.01) |
| F26B 5/06 | (2006.01) |

(52) U.S. Cl.
CPC .......... G01N 33/0032 (2013.01); G01L 21/12 (2013.01); *F26B 5/06* (2013.01); *F26B 25/22* (2013.01)

(58) Field of Classification Search
CPC . F26B 5/06; F26B 25/22; G01L 15/00; G01L 21/22; G01N 33/0032
See application file for complete search history.

(56) References Cited

U.S. PATENT DOCUMENTS

| | | | |
|---|---|---|---|
| 3,192,643 A | 7/1965 | Rieutord | |
| 3,262,212 A | 7/1966 | De Buhr | |
| 4,142,303 A * | 3/1979 | Fraser | F26B 5/06 |
| | | | 34/92 |
| 5,452,613 A * | 9/1995 | Bills | G01L 21/02 |
| | | | 73/706 |

(Continued)

FOREIGN PATENT DOCUMENTS

WO    WO2011/077390 A2    6/2011

OTHER PUBLICATIONS

SP Scientific, "Basic Principles of Freeze Drying" as downloaded by the Internet Archive Wayback Machine on Dec. 20, 2016; http://www.spscientific.com/freeze-drying-lyophilization-basics/.*

(Continued)

*Primary Examiner* — Justin N Olamit
(74) *Attorney, Agent, or Firm* — Hamilton, Brook, Smith & Reynolds, P.C.

(57) ABSTRACT

A partial pressure detector and methods of detecting a partial pressure are provided, in which a thermal conductivity gauge, such as a Pirani gauge, is configured to sense a pressure of a mixture of gases within a vacuum chamber. An input of the partial pressure detector is configured to receive a total pressure reading from a species-independent pressure sensor of the mixture of gases in the vacuum chamber, and a controller configured to provide an output representing an amount of a species of gas in the vacuum chamber as a function of the pressure as sensed by the thermal conductivity gauge and the received total pressure reading. The (Continued)

controller has a resolution, and a range of the resolution is scaled to a range of expected partial pressures of the species. The output can be a partial pressure or a weighted partial pressure of the gas species.

34 Claims, 9 Drawing Sheets

(56) References Cited

U.S. PATENT DOCUMENTS

| | | | |
|---|---|---|---|
| 7,706,995 B2* | 4/2010 | Sullivan | G01L 9/0072 |
| | | | 702/85 |
| 2006/0107898 A1* | 5/2006 | Blomberg | C23C 16/52 |
| | | | 118/715 |
| 2011/0209554 A1 | 9/2011 | Miyashita | |
| 2015/0125839 A1* | 5/2015 | Tillges | A61B 5/1038 |
| | | | 434/262 |
| 2019/0316948 A1* | 10/2019 | Karol | A61M 1/28 |

OTHER PUBLICATIONS

Patel et al., "Determination of End Point of Primary Drying in Freeze-Drying Process Control", AAPS PharmSciTech, vol. 11, No. 1, Mar. 2010, pp. 73-84.*

International Search Report and Written Opinion for International Application No. PCT/US2019/030545, entitled "Methods and Apparatus for Multiple Channel Mass Flow and Ratio Control Systems," dated Jul. 11, 2019.

* cited by examiner

METHOD AND APPARATUS FOR PARTIAL PRESSURE DETECTION

BACKGROUND

Lyophilization is an expensive and lengthy process used throughout the pharmaceutical industry to freeze dry labile chemicals. Lyophilization, also referred to as freeze drying, is the removal of water or other solvents from a product by sequential freezing (Thermal Treatment), vacuum sublimation (Primary Drying), and vacuum desorption (Secondary Drying). Lyophilization can provide products having shelf lives that significantly exceed those of air dried product. Most lyophilization systems operate without sensors to provide water content measurements during operation. As a result, primary and secondary drying times within a lyophilization process are selected during process development and are not adjusted on a process-by-process basis. Such fixed drying times can result in product that is not completely dried or, alternatively, in wasted time during production due to over-drying. As part of Process Analytical Technology (PAT) initiatives under development in the pharmaceutical industry, methodologies for detecting endpoints of primary and secondary drying processes, as well as sensors to be used in such methodologies, are increasingly being included in lyophilization systems.

SUMMARY

Partial pressure detectors and methods of detecting a partial pressure of a gas species are provided. Such devices and methods can be used for detecting a partial pressure of water or other solvent during lyophilization processes at a higher step resolution than that of conventional Pirani gauges. Such devices and methods can advantageously provide for more accurate endpoint detection, particularly for secondary drying processes where low levels of water content are achieved.

A partial pressure detector includes a thermal conductivity gauge, such as a Pirani gauge, configured to sense a pressure of a mixture of gases within a vacuum chamber and an input configured to receive a total pressure reading from a species-independent pressure sensor of the mixture of gases in the vacuum chamber. The partial pressure detector further includes a controller configured to provide an output proportional to a partial pressure of a species of gas in the vacuum chamber as a function of the pressure as sensed by the thermal conductivity gauge and the received total pressure reading. The controller can have a resolution scaled to a range of expected partial pressures of the species.

The partial pressure detector can further include a housing, which contains the controller and at least partially contains the thermal conductivity gauge. The thermal conductivity gauge can be configured to sense a thermal response of a sensor wire to a mixture of gases within a vacuum chamber.

A method of detecting a partial pressure includes, with a thermal conductivity gauge, such as a Pirani gauge, sensing a pressure of a mixture of gases within a vacuum chamber, and, with a species-independent pressure sensor, sensing a total pressure of the mixture of gases within the vacuum chamber. The method further includes providing an output proportional to a partial pressure of a species of gas in the vacuum chamber as a function of the pressure as sensed by the thermal conductivity gauge and the total pressure as sensed by the species-independent pressure sensor. The output is provided by a controller having a resolution scaled to a range of expected partial pressures of the species.

The function can include a difference in pressure between the determined pressure and the received total pressure reading, such as the function according to the following:

$$\Delta TP = TP_{PG} - TP = xPP_S \quad (1),$$

where $\Delta TP$ represents a weighted partial pressure of the species; $TP_{PG}$ is the pressure as sensed by the thermal conductivity gauge (e.g. a Pirani gauge), TP is the total pressure as received from the species-independent pressure sensor, x is a species-dependent factor, and $PP_S$ is the partial pressure of the species. The output can represent a weighted partial pressure of the gas species in the chamber (e.g., $\Delta TP$), a partial pressure of the gas species in the chamber (e.g., $PP_S$), such as can be provided by the following rearrangement of the function of Eqn. 1:

$$PP_S = \frac{TP_{PG} - TP}{x}, \quad (2)$$

or both. If the species is water, the species-dependent factor can be about 0.4.

The controller can be further configured to provide a second output, the second output representing a total pressure of the mixture of gases within the vacuum chamber as determined based on the sensed thermal response of the thermal conductivity gauge. The controller can be further configured to adaptively average the output, including an output representing the partial pressure of the species and/or the total pressure.

The species-independent pressure sensor can be a capacitance diaphragm gauge or other type of capacitance manometer. Alternatively, the species-independent pressure sensor can be a piezoresistive diaphragm (PRD) gauge, a fiber-optic diaphragm deflection gauge, or a fiber Bragg grating (FBR) sensor. The partial pressure detector can include an input port configured to connect to an output of the species-independent pressure sensor. Alternatively, the partial pressure detector can include the species-independent pressure sensor, For example, the species-independent pressure sensor can be contained, or partially contained, within a housing together with the thermal conductivity gauge.

The partial pressure detector can further include a trigger configured to zero the output of the controller, providing for calibration to more accurate sensors, such a species-independent sensor connected to a same vacuum chamber.

The species can be a solvent of a sample undergoing lyophilization in the vacuum chamber, such as water, or a mixture of solvents. For example, the species can include water and a co-solvent, such as tert-butanol. The mixture of gases in the vacuum chamber can be a binary mixture. Alternatively, the mixture of gases can include more than two gases, provided that the mixture includes at least one gas having a different thermal conductivity than the others.

Thermal conductivity gauges are one type of species-dependent pressure gauges. In the pressure detectors and methods of detecting a partial pressure described above, a species-dependent gauge can be included that is configured to sense a pressure of a mixture of gases within a vacuum chamber. Examples of species-dependent gauges include thermal conductivity gauges, such as Pirani sensors, thermocouple gauges, ionization gauges, spinning rotor gauges, resonating pressure sensors, and photonic pressure sensors. Furthermore, partial pressure detectors and methods of detecting partial pressure can include any combination or permutation of the features described herein.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

DETAILED DESCRIPTION

A description of example embodiments follows.

Partial pressure detectors and methods of detecting a partial pressure of a gas species are provided. Such devices and methods can be used for detecting a partial pressure of water or other solvent during lyophilization processes with a step resolution greater than that provided by conventional Pirani gauges. Such devices and methods can advantageously provide for more accurate endpoint detection.

Figure 1:
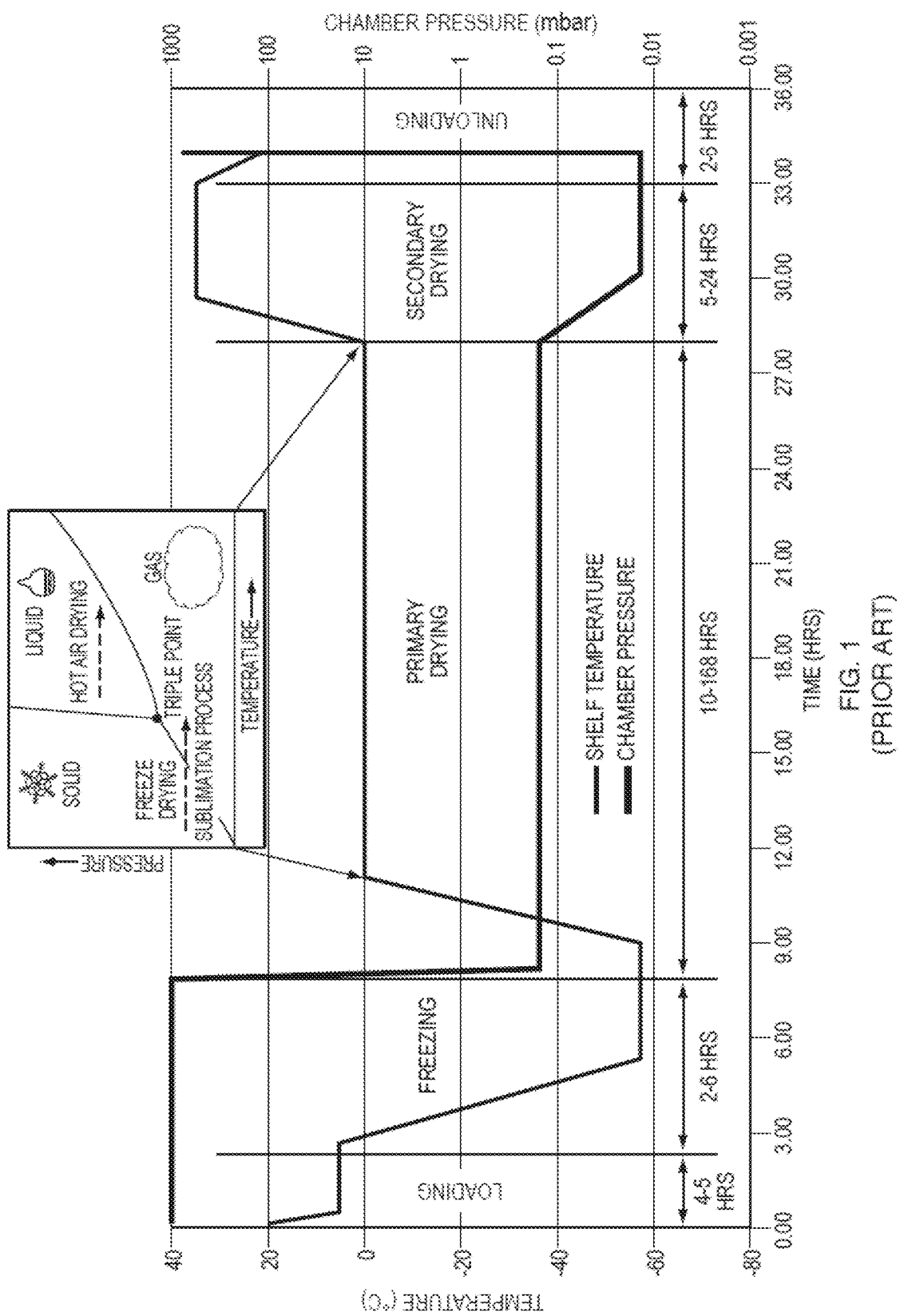
FIG. 1 is a graph illustrating a prior art lyophilization process.

A typical lyophilization process is illustrated in FIG. 1. During an initial loading process, samples are placed in a lyophilization chamber. The samples are typically vials, flasks, or trays that contain a drug product (e.g., proteins, microbes, pharmaceuticals, tissues, or plasmas). The samples are then frozen in a process that can take about 2 to about 6 hours. Following the initial loading and freezing steps, the drying processes begin. During a primary drying process, frozen water (and other solvents) are removed from the product through sublimation. Sublimation is the process of changing from a solid to a gas without passing through an intermediate liquid phase. As shown in FIG. 1, sublimation occurs at pressures and temperatures that are below the triple point of water. To initiate the primary drying process, a vacuum is applied to the lyophilization chamber, causing pressure within the chamber to drop, and heat energy is added, causing the product to sublime. The sublimation process can take about 10 to about 168 hours, depending upon the size of the chamber, the number of samples contained in the chamber, and the water content of the samples. A majority of the water content of the samples is removed during the primary drying process.

A secondary drying process follows in which bound water molecules are removed by desorption. As shown in FIG. 1, during the secondary drying process, pressure within the chamber is again lowered, while additional heat is applied, causing bound water molecules to be released from the product. Because free ice within the sample has been removed during the primary drying process, the temperature may be increased during the secondary drying process without causing the product to melt or collapse. The desorption process can take about 5 to about 24 hours. After both drying processes have completed, the samples are unloaded from the chamber.

An important consideration in lyophilization processes is the determination of endpoints for both the primary and secondary drying stages. Moisture content can be in the range of, for example, about 5% to about 10%, at the end of a primary drying process and in the range of about 0.5% to about 3% at the end of a secondary drying process. The application of additional heat too early in a lyophilization process (e.g., before sublimation has completed) can cause melting or collapse of the product (often referred to as "cake collapse"). However, cost considerations make it undesirable to unnecessarily extend the time of a primary drying process. Also, various drugs may have different thresholds for acceptable residual moisture content. Generally, a longer shelf-life can be achieved by removing more moisture. However, some biological products can be over-dried if moisture content is brought below an acceptable threshold.

One methodology for detecting the endpoints of the drying processes involves the measurement of sample vial temperatures with thermocouples, such as wired or wireless thermocouples, during the drying process. An increase in sample temperature is expected when the frozen water is removed because the heat applied to the sample is no longer being removed by sublimation of water. However, such an approach has a main disadvantage in that thermocouples that contact the sample can affect the nucleation of the product in the vial, providing a false indication of completion of the drying process, (i.e., not a bulk measurement).

Another approach involves the measurement of water content in the chamber during the drying process. Methodologies for this approach include the use of additional sensors that are capable of detecting water in the system, such as Pirani gauges, plasma emitters, and residual gas analyzers. One method, in particular, involves the use of a combination of capacitance diaphragm gauges, alternatively referred to as capacitance manometers, and Pirani gauges to measure water content during primary and second drying processes. This methodology, further described in Patel, Sajal M., Takayuki Doen, and Michael J. Pikal. "Determination of End Point of Primary Drying in Freeze-Drying Process Control." AAPS PharmSciTech 11.1 (2010): 73-84, has been found to minimize wasted time during lengthy primary drying processes. This methodology is often called Comparative Pressure Measurement (CPM) and is suited to lyophilization processes in which the total pressure in the system is kept constant.

In constant pressure lyophilization processes, pressure is monitored with a capacitance diaphragm gauge and, as water vapor pressure drops during the drying process, an inert gas such as nitrogen is introduced into the system as needed to maintain a constant total pressure. Constant pressure lyophilization provides a continuous rate of heat exchange between the sample vials contained in the lyophilization chamber and the gas phase, providing for faster drying process cycles, particularly for primary drying processes. As such, constant pressure lyophilization methods are gaining traction in the industry, and the CPM methodology provides for the ability to detect drying process endpoints in constant pressure systems, as described in more detail below.

Figure 2:
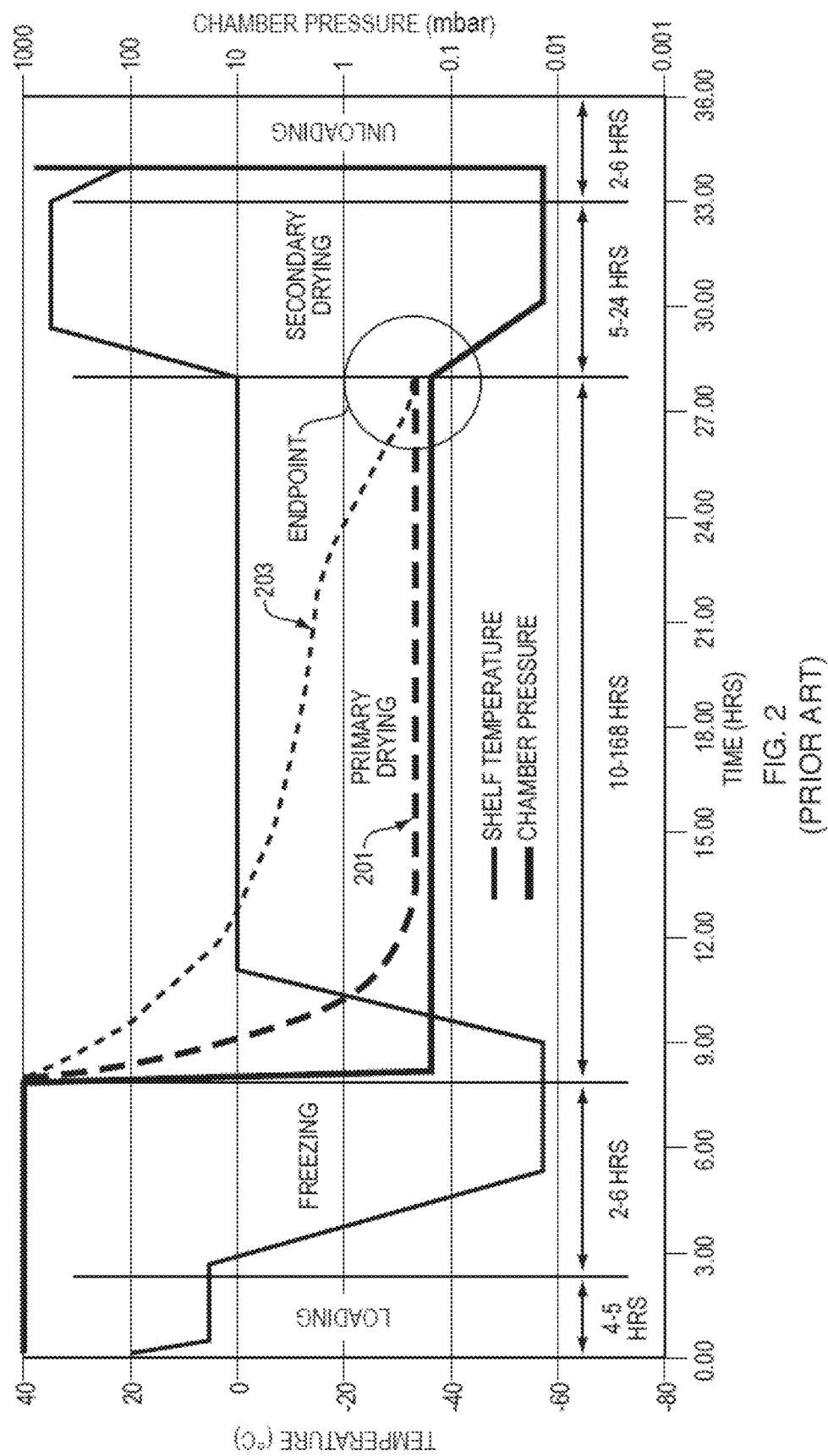
FIG. 2 is a graph illustrating a prior art approach to detecting an endpoint of a primary drying process.

The pressure responses of a Pirani gauge and a capacitance diaphragm gauge during a constant pressure lyophilization process are shown in FIG. 2, where the species independent capacitance manometer output 201 and the water vapor sensitive Pirani gauge output 203 are superimposed over the process diagram of FIG. 1. As shown in FIG.

2, the Pirani gauge readings initially overestimate the total pressure while the gas composition is dominated by water but eventually match the readings of the capacitance diaphragm gauge as water is removed from the chamber and the gas composition becomes dominated by nitrogen.

Figure 3:
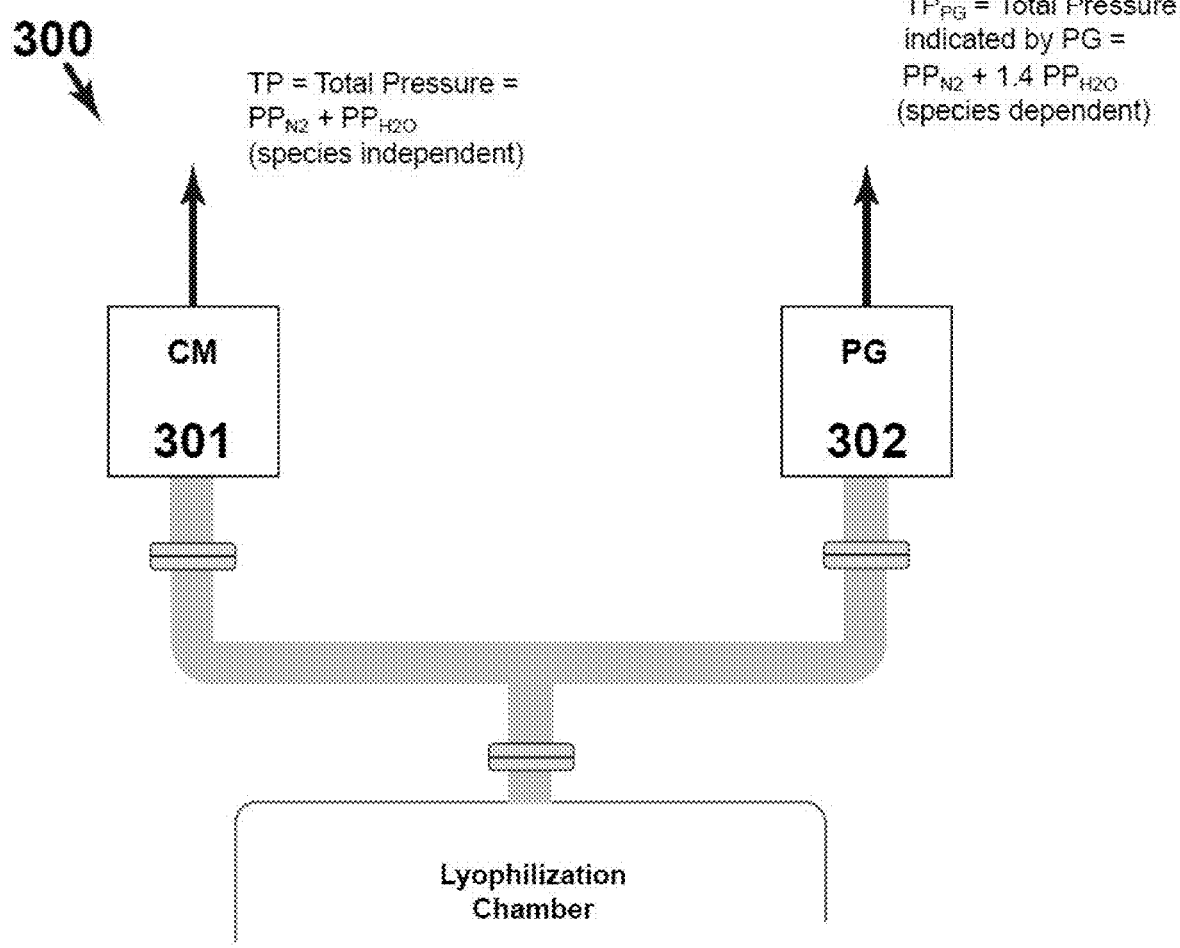
FIG. 3 is a diagram of a constant pressure lyophilization system.

A diagram of a constant pressure lyophilization system 300 is shown in FIG. 3. A total pressure (TP) of gases within the lyophilization chamber is measured by a capacitance manometer (CM) 301 as well as by a Pirani gauge (PG) 302. Because the capacitance manometer is species independent, its total pressure reading can be given by the following sum of partial pressures:

$$TP = PP_{N2} + PP_{H2O} \tag{3}$$

The Pirani gauge, which is calibrated for pure $N_2$, overestimates the water pressure readings by about 40%. As such, the total pressure reported by the Pirani gauge can be given by the following sum of partial pressures, in which the partial pressure of water is weighted to account for overestimation by the Pirani gauge:

$$TP_{PG} = PP_{N2} + 1.4 PP_{H2O} \tag{4}$$

Once water is eliminated from the system and the gas in the lyophilization chamber is pure $N_2$, it is expected that the CM and PG readings (i.e., TP and $TP_{PG}$, respectively) will be in agreement as both sensors are calibrated against pure $N_2$. Thus, during CPM processes, the pressure readings TP and $TP_{PG}$ are compared, and the drying process is said to end when the two readings converge, as shown in FIG. 2, or when a ratio between the two values is equal to 1.

One of the main advantages of CPM techniques is that Pirani gauges are not destructive to samples, unlike thermocouples. Pirani gauges, a type of thermal conductivity gauge, are known in the art and measure absolute pressure by determining heat loss from a heated sensor wire. Conventional Pirani gauges include a Wheatstone bridge in connection with a sensor wire that is maintained at a constant temperature. The electrical power required to keep the sensor wire at a constant temperature is used to provide a measure of pressure.

Figure 4A:
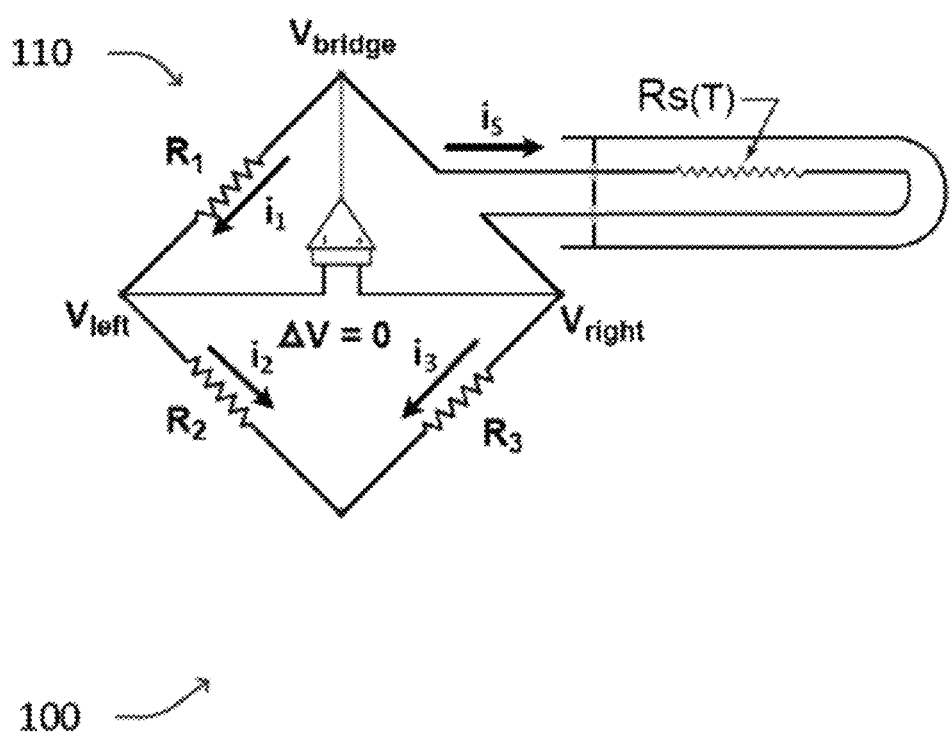
FIG. 4A is a circuit diagram of a prior art Pirani gauge.

An example of a conventional Pirani gauge 100 is illustrated in the circuit diagram of FIG. 4A. The sensor comprises a temperature sensitive resistance $R_S$ connected as one arm of a Wheatstone bridge 110. $R_3$ is typically a temperature sensitive resistance designed to have a negligible temperature rise due to the current $i_3$. $R_2$ and $R_1$ are typically fixed resistances. The sensor wire $R_S$ and, typically, $R_3$ are exposed to the environment in which a pressure is to be measured. The sensor wire $R_S$ may extend within an envelope.

The resistance values of resistors $R_1$, $R_2$ and $R_3$ are selected such that when a pressure-dependent voltage $V_{bridge}$ is applied to the top of the bridge, at which $V_{left} = V_{right}$, the resistance of the sensor wire $R_S$ is fixed and identical to $(R_1 * R_3)/R_2$. Voltage $V_{bridge}$ can be automatically controlled by an operational amplifier to maintain the voltage difference between $V_{left}$ and $V_{right}$ at zero volts. When the potential drop from $V_{left}$ to $V_{right}$ is zero, the bridge is considered to be balanced. At bridge balance, the following conditions exist:

$$i_s = i_3, \tag{5}$$

$$i_1 = i_2, \tag{6}$$

$$i_s \cdot R_S = i_1 \cdot R_1, \tag{7}$$

$$i_2 \cdot R_2 = i_3 \cdot R_3, \tag{8}$$

Dividing Eqn. 7 by Eqn. 8 and using Eqn. 5 and 6 provides the following:

$$R_S = \beta R_3, \tag{9}$$

where $$\beta = R_1 \cdot R_2, \tag{10}$$

Thus, at bridge balance, $R_S$ is a constant fraction $\beta$ of $R_3$. To achieve a steady-state condition in $R_S$ at any given pressure, the following equation must be satisfied: Electrical power input to $R_S$=Power radiated by $R_S$+Power lost out ends of $R_S$+Power lost to gas by $R_S$.

Figure 4B:
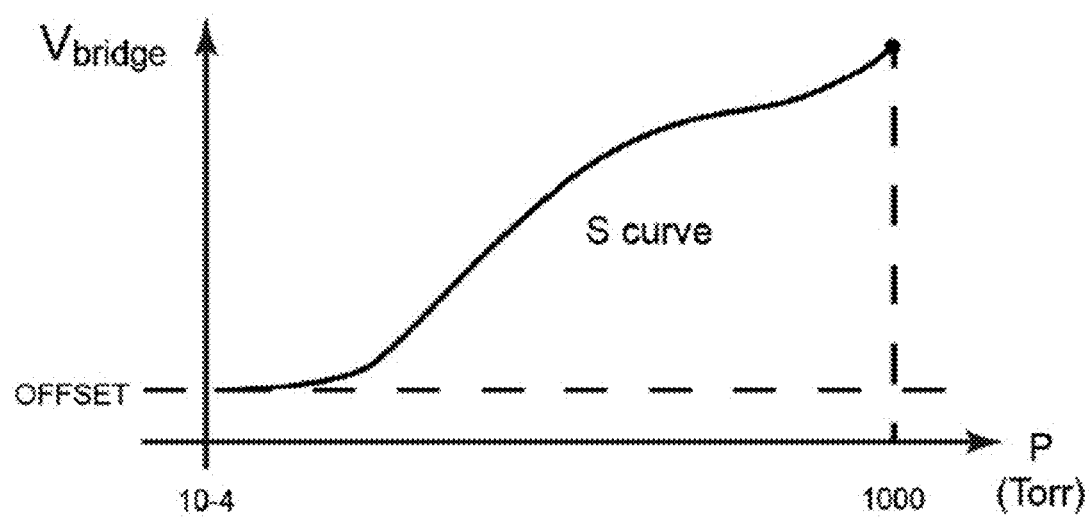
FIG. 4B is a graph illustrating a response of the Pirani gauge of FIG. 4A.

Because the amount of electrical power required to keep the sensor resistor $R_S$ at a constant temperature and a constant resistance increases with pressure, voltage $V_{bridge}$ depends on pressure as well. This relationship is illustrated in FIG. 4B, which is an example plot of voltage $V_{bridge}$ over a range of pressure within a chamber occupied by $R_S$. As shown, the voltage $V_{bridge}$ exhibits an S-curve over the pressure range. A conventional Pirani gauge is calibrated against several known pressures to determine a relationship between unknown pressure, $P_x$, and the power loss to the gas, or more conveniently, to the bridge voltage. Then, assuming end losses and radiation losses remain constant, the unknown pressure of the gas $P_x$ may be directly determined by the power lost to the gas or related to the bridge voltage at bridge balance.

As such, Pirani gauges, such as gauge 100, provide a simple configuration for measuring pressure. However, Pirani gauges are not as accurate as capacitance diaphragm gauges (CDGs). As a result, the use of Pirani gauges presents challenges for metrology labs in pharmaceutical industries that require measurement accuracies matching those provided by CDGs. Additionally, metrology labs are not well versed in calibration procedures for Pirani gauges and often do not have adequate experience to determine how often such gauges need to be calibrated or when such gauges show signs of inaccuracy. Presently, Pirani gauges used for CPM processes in lyophilization systems have accuracies of roughly 15%, while capacitance diaphragm gauges have accuracies of roughly 0.25% or better. If a difference in accuracy between a Pirani gauge and capacitance diaphragm gauge is not accounted for, or if the Pirani gauge is not properly calibrated, inconsistencies in end point detection can result. The difference in accuracy between a Pirani gauge and a capacitance diaphragm gauge requires routine recalibration of the Pirani gauge to account for both accuracy and drift.

Pirani gauges can also provide inadequate output signals (e.g., S-curves), which creates difficulties for system integrators in the pharmaceutical industry to incorporate the gauges into the data acquisition systems of these tools. The Pirani gauges currently used in CPM processes have limited pressure resolution, and as such, lack the ability to detect small changes in water levels. The lack of step resolution in an analog pressure output of the Pirani gauge limits water detection capabilities, particularly at the end of secondary drying processes where low water levels are achieved.

For example, a conventional Pirani gauge used in a constant pressure lyophilization process may have an output resolution of ±10 mV. The step resolution of such a gauge, assuming a logarithmic analog output and 1V/decade, can be given by the following, where P is pressure and V is voltage:

$$\Delta P = \frac{\Delta V \cdot P}{2.3}. \tag{11}$$

Thus, for a process conducted at a pressure of 0.1 Torr, the step resolution of the conventional Pirani gauge is ±4.3E-4 Torr, as shown by populating Eqn. 11 as follows:

$$\Delta P = \frac{(10 \cdot 10^3) \cdot 0.1}{2.3} = 4.3E\text{-}4 \; Torr. \quad (12)$$

A step resolution of ±4.3E-4 Torr is considered inadequate as it does not provide for adequate detection limits and, furthermore, does not match the four decades of dynamic range provided by capacitance diaphragm gauges.

Some commercially available Pirani gauges are able to provide for higher resolutions. For example, a Pirani gauge having a 10V scale and a 16 bit digital to analog converter (DAC) can be programmed to provide a linear analog output that is scaled to a pressure range of 0-0.1 Torr. The step resolution of such a gauge can be given by the following:

$$\Delta P = \frac{10V \cdot 0.1 \; Torr}{10V \cdot 2^{16}} = 1.5E\text{-}6 \; Torr. \quad (13)$$

Such a Pirani gauge offers the advantages of an improved step resolution that is more appropriate for lyophilization processes and, given the linear output, a simple relationship between voltage and pressure. However, there still exists a significant difference in accuracy between Pirani sensors and capacitance diaphragm gauges and a need for gauges that can provide for even greater step resolutions.

Pressure detectors are provided that include Pirani sensors and that are configured to provide an output representing a partial pressure of a gas species based upon the Pirani sensor reading and a reading from a species independent pressure sensor, such as a capacitance diaphragm gauge. Such partial pressure detectors can advantageously provide for increased step resolution with respect to pressure measurements indicative of water content, in turn allowing for improved detection of small changes in water levels during lyophilization processes. Such partial pressure detectors can also include a trigger for zeroing a differential output of the partial pressure detector, providing for easy calibration to a species-independent pressure sensor, such as a capacitance diaphragm gauge.

Figure 5A:
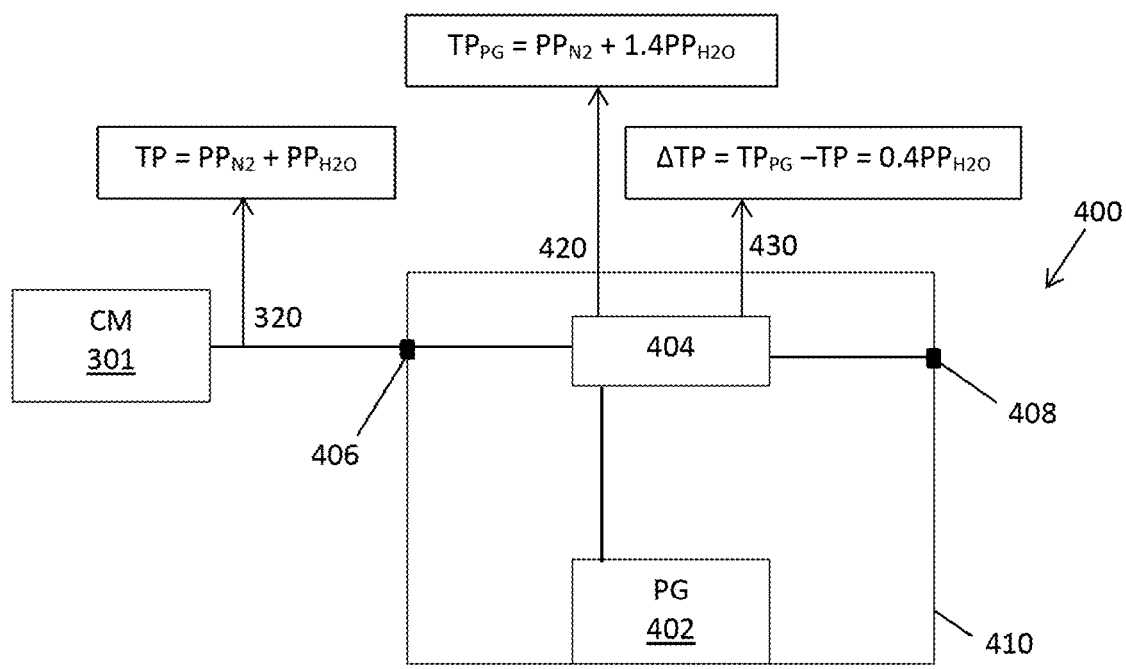
FIG. 5A is a diagram of a partial pressure detector.

An example of a partial pressure detector 400 is shown in FIG. 5A. The partial pressure detector 400 includes a Pirani gauge 402, alternatively referred to as a Pirani sensor, a controller 404, and a pressure input port 406 that receives a total pressure reading from a species independent pressure sensor, such as a capacitance manometer 301. A housing 410 can enclose the controller 404 and at least a portion of the Pirani sensor 402.

The pressure input port 406 can provide for an analog or digital connection to the capacitance manometer 301 such that total pressure readings from the capacitance manometer 301 can be provided to the controller 404 on a continuous basis. If the reading is provided digitally, the controller 404 can directly query the capacitance manometer for the pressure. If analog, the controller 404 can be provided with a range of pressures of the capacitance manometer to equate a signal from the capacitance manometer to a pressure.

As illustrated in FIG. 5A, an output 320 of the capacitance manometer 301 provides a species-independent total pressure reading (TP) that, in a conventional constant-pressure lyophilization system, represents the added partial pressures of $N_2$ gas and water vapor. As described above, Pirani gauges provide a total pressure reading ($TP_{PG}$) that is species-dependent and that will overestimate a total pressure in the presence of water.

The partial pressure detector 400 is configured to provide a differential output 430 in place of, or in addition to, an absolute output 420 of the Pirani gauge. With Eqns. 3 and 4, repeated below for convenience, $$TP = PP_{N2} + PP_{H2O} \quad (3),$$

$$TP_{PG} = PP_{N2} + 1.4 PP_{H2O} \quad (4),$$

it can be shown that a difference ($\Delta TP$) between the pressure readings of the Pirani sensor 402 ($TP_{PG}$) and the capacitance manometer 301 (TP) provides for an output that is proportional to a partial pressure of water in the system:

$$\Delta TP = TP_{PG} - TP = 0.4 PP_{H2O} \quad (14).$$

Figure 5B:
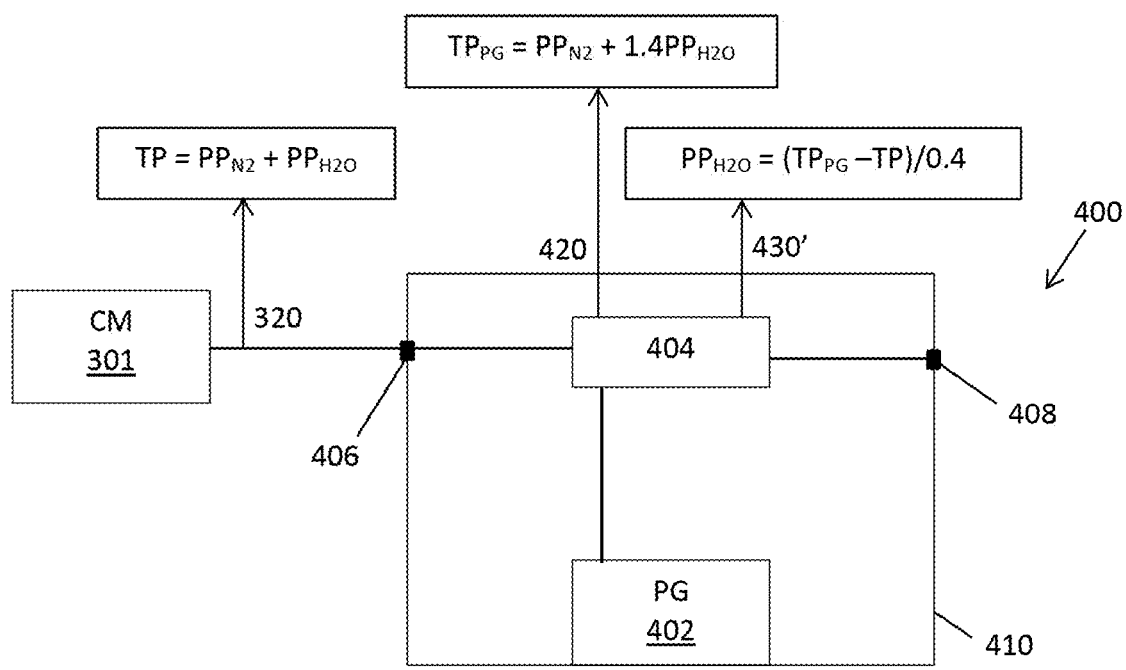
FIG. 5B is a diagram of another partial pressure detector

As shown in FIG. 5A, the output 430 can be configured to provide $\Delta TP$, which represents a weighted partial pressure of water (e.g., weighted by a factor of 0.4, the factor being indicative of an amount by which the Pirani gauge overestimates water content). Alternatively, or in addition, the partial pressure of water ($PP_{H2O}$) can be provided, as shown in FIG. 5B with output 430'. An output representing $PP_{H2O}$ can be provided by accounting for the factor of 0.4 for water. In particular, rearranging Eqn. 14, a direct measurement of $PP_{H2O}$ can be provided according to the following:

$$PP_{H2O} = \frac{TP_{PG} - TP}{0.4}. \quad (15)$$

As such, the differential outputs 430, 430' of the partial pressure detector 400 provide for a direct measurement of an amount of water in a constant-pressure lyophilization system.

The output resolution of the partial pressure detector 400 can be scaled to an expected range of partial pressures of water as opposed to being scaled to a range of total pressures. Such scaling can provide for increased step resolution with respect to pressure measurements that are most relevant to lyophilization process endpoints.

For example, considering a constant pressure lyophilization process that occurs at 0.1 Torr and has a maximum water content of 20% at the start of the process, the maximum partial pressure of water during the process ($PP_{H2O}$) is expected to be 0.02 Torr. At this maximum partial pressure, the output of the partial pressure detector 400 of FIG. 5A, using Eqn. 14, is 0.008 Torr. The output of the partial pressure detector can be scaled to a pressure range of 0 to 0.01 Torr, as opposed to the pressure range of 0 to 0.1 Torr required for reporting total pressure measurements. Assuming, for example, that the partial pressure detector has a 10V scale, a 16 bit digital to analog converter (DAC), and provides a linear analog output scaled to a pressure range of 0 to 0.01 Torr, the step resolution of such a gauge can be given by the following:

$$\Delta P = \frac{10V \cdot 0.01 \; Torr}{10V \cdot 2^{16}} = 1.5 \; E\text{-}7 \; Torr. \quad (16)$$

As such, the differential output of a partial pressure detector can provide a signal that is directly proportional to the partial pressure of water at an improved step resolution that is adequate for lyophilization processes, including secondary drying processes. In the example above, by scaling the analog output such that the entire range of the DAC is used for a smaller pressure range (e.g., 0-0.01 Torr), 100 times more resolution can be obtained than that of conventional Pirani gauges scaled to larger pressure ranges (e.g., 1.1-1.2 Torr) for the reporting of absolute pressure. While the example above describes an analog signal implementation, it is also possible to instead provide a differential pressure measurement by a digital communication port. The differential output of a partial pressure detector may initially be saturated (e.g., reporting a partial pressure or weighted partial pressure at an upper end of the pressure range to which the detector is scaled when the pressure may, in fact, be greater). However, as water concentration approaches zero, the differential output is able to report actual partial pressures or weighted partial pressures of water at a step resolution that is greater than that which could be provided by reporting total pressures. In such instances, an output of the partial pressure detector can be switched between reporting a total pressure (e.g., output 420) at the start of a process, and a partial pressure or weighted partial pressure (e.g., output 430, 403') toward the end of the process. For example, the total pressure and partial pressure outputs may be multiplexed within the detector. Furthermore, while a linear output is described, the partial pressure detector can instead provide a logarithmic output.

The partial pressure detector can further include a trigger 408 for zeroing the differential output, which provides for a straightforward calibration procedure to discipline the output of the Pirani gauge to a more accurate species-independent gauge, such as a capacitance diaphragm gauge.

Figure 6:
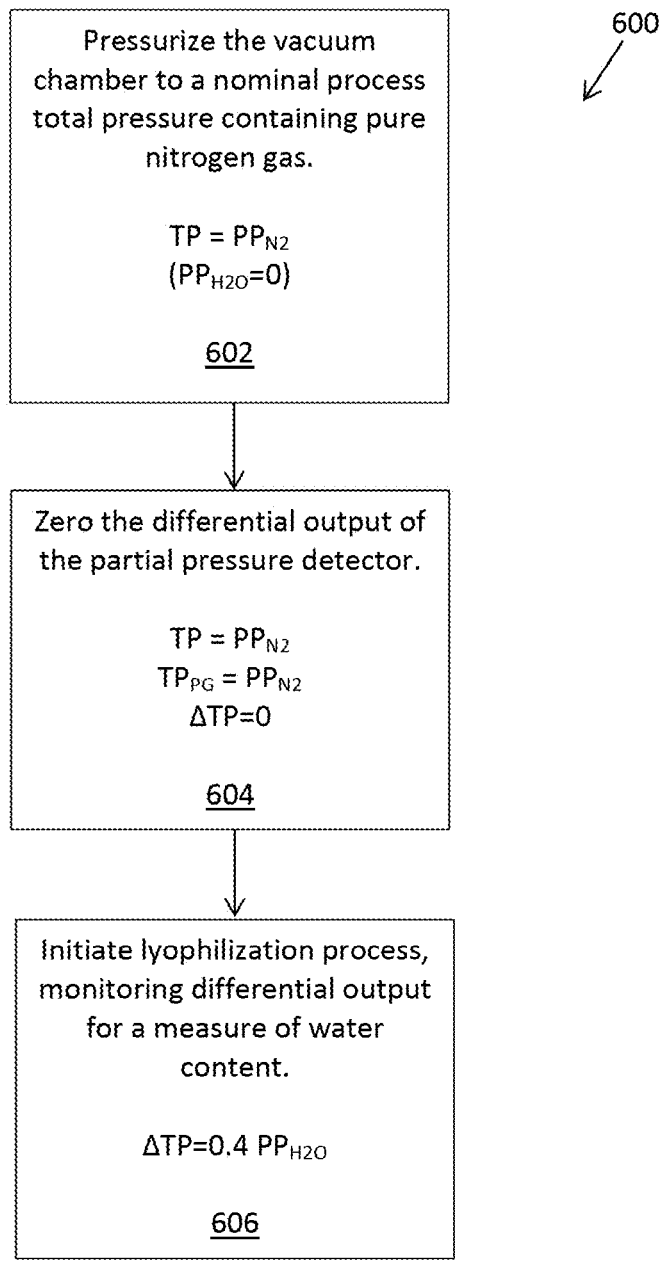
FIG. 6 is a flowchart of a calibration process.

An example of a process 600 for calibrating a partial pressure detector prior to lyophilization is shown in FIG. 6. Initially, the vacuum chamber is pressurized to a nominal process total pressure without any water present (step 602). The differential output of the partial pressure detector can then be zeroed, and an accuracy offset can be stored for $\Delta TP=0$ in the presence of pure nitrogen gas at process pressure (step 604). The lyophilization process can then be initiated, with the differential output providing a measure of water content in the vacuum chamber (step 606). By zeroing the differential output at the beginning of a process, differences in accuracy between the Pirani gauge and the capacitance diaphragm gauge can be accounted for, as well as differences that may result from drift that can occur over time.

The calibration procedure of FIG. 6 can be performed at the start of any process, including after completion of a primary drying process and prior to initiation of a secondary drying process, where the high resolution provided by the partial pressure detector is most beneficial given the low water content levels of secondary drying processes. Alternatively, or in addition, valving can be included that isolates both gauges from the lyophilization chamber and exposes the gauges 301, 402 to pure $N_2$ at process pressure. With such valving, the partial pressure detector can be calibrated while the lyophilization chamber remains occupied by product samples.

The Pirani gauge included in the partial pressure detectors 400, 400' can have any type of Pirani sensor configuration, including that of, for example, the Pirani gauge illustrated in FIG. 4A. Other configurations of Pirani sensors and other types of thermal conductivity gauges are also possible and are known in the art. Examples of thermal conductivity gauges that can be included in partial pressure detectors include those described in U.S. Pat. Nos. 6,799,468; 6,938,493; and 7,249,516, the entire contents of which are incorporated herein by reference. Examples of Pirani gauges include the 901P Loadlock Vacuum Transducer, the 905 MicroPirani™ Ultra Compact Vacuum Sensor, the 925 MicroPirani™ Vacuum Transducer, the 275 Mini-Convectron® Module, and the 275 Convectron Pirani Vacuum Gauge (MKS Instruments, Andover Mass.).

Figure 7:
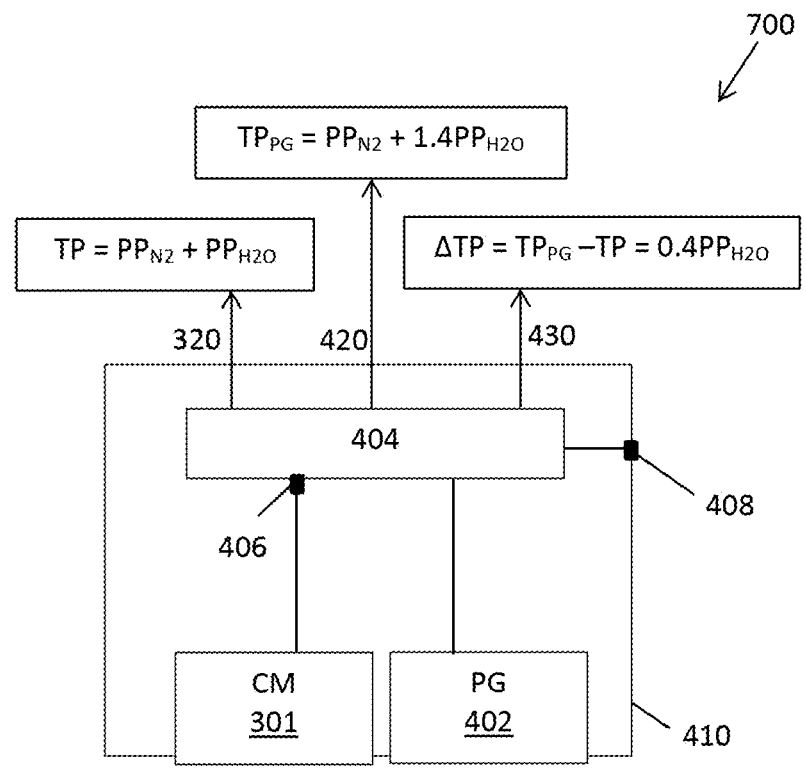
FIG. 7 is a diagram of yet another partial pressure detector.

As illustrated in FIGS. 5A-B, the housing 410 encloses the controller 404 and at least a portion of the Pirani gauge 402, with the port 406 providing for connection to a capacitance manometer 301 external to the housing. However, the capacitance manometer 301 can alternatively be included within the housing 410 such that the partial pressure detector comprises both types of gauges, as shown by the partial pressure detector 700 of FIG. 7.

While capacitance manometers, specifically capacitance diaphragm gauges, have been described as being the species-independent pressure sensors of the example devices and methods above, other species-independent pressure sensors can be included in place of, or in addition to capacitance manometers. For example, partial pressure detectors can include a piezoresistive diaphragm (PRD) gauge, a fiber-optic diaphragm deflection gauge, and/or a fiber Bragg grating (FBR) sensor.

In addition to reporting a partial pressure, the controller 404 of a partial pressure detector can be configured to provide for adaptive averaging of any of TP, $TP_{PG}$, and $\Delta TP$, or a combination thereof. By increasing the amount of averaging as $PP_{H2O}$ approaches zero, pressure measurement resolution can be further improved.

While the partial pressure detector has been described with respect to a lyophilization process involving nitrogen gas as the process gas and water vapor as the species to be detected, other combinations of process gases and solvent gases are possible. Generalizing Eqn. 14, a differential output can be provided according to the following:

$$\Delta TP = TP_{PG} - TP = xPP_S \quad (1),$$

where $PP_S$ is the partial pressure of the species of gas to be detected, which can comprise other solvents in place of, or in addition to, water, and x is a species-dependent factor. Rearranging Eqn. 1, a direct measurement of the species of gas can be provided by the following:

$$PP_S = \frac{TP_{PG} - TP}{x}. \quad (2)$$

In some instances, water may be the only solvent present in a sample. However, for products that are not miscible in water, other solvents may be included in place of water, or co-solvents may be included together with water.

For example, tert-butanol is a non-aqueous co-solvent that is often included in drug preparations. The inclusion of tert-butanol, typically forming 10% of a solvent mixture, can facilitate sublimation of the drug sample. As both water and tert-butanol have a higher thermal conductivity than nitrogen, the partial pressure detector can still provide a differential output representative of an amount of solvent present in the system. Furthermore, co-solvents typically used in drug preparations have a high vapor pressure relative to water and, therefore, may be sublimated out of the sample earlier in the lyophilization process. As such, a composition of the sublimated gas may be time-dependent, with different species contributing to the differential output at different timepoints throughout the process.

Provided that a species-dependent factor for the solvent, co-solvent, or solvent mixture is known, a direct measurement of the solvent gas can be provided according to Eqn. 2. Nonetheless, even if the species dependent factor is unknown, a differential output according to Eqn. 1 can still be representative of an amount of solvent remaining in the system, and as such, can still be used to determine an endpoint of the lyophilization process, even where the gas mixture is non-binary.

While example partial pressure detectors, such as detectors 400 and 700, have been described to include thermal conductivity gauges, such as Pirani sensors, other species-dependent sensors can instead be included, such as thermocouple gauges, ionization gauges, spinning rotor gauges, resonating pressure sensors, and photonic pressure sensors. Provided that the species-dependent gauge exhibits a response that differs from that of the species-independent sensor (e.g., a capacitance manometer) in the presence of the species being monitored, a differential output can be provided that represents an amount of the species remaining in a system.

In addition to lyophilization, other processes that involve binary gas analysis can benefit from partial pressure detectors, such as detector 400. In particular, the purity of a binary gas mixture can be assessed where the impurity has a different thermal conductivity than the main gas. For example, a partial pressure detector can be used to detect air contamination in helium gas. For such processes, the partial pressure detector can be calibrated at the start of the process for the main gas, as described above with regard to $N_2$ for lyophilization processes. The impurity can be the species for which a partial pressure is measured.

Partial pressure detectors can also be used to confirm a proper composition of a binary gas mixture used in a reactive sputtering process. For example, Ar and $O_2$ ratios are typically carefully controlled during reactive sputtering processes, and partial pressure detection can advantageously provide for finer monitoring of one species. Other examples of reactive sputtering compositions include nitrogen-methane and nitrogen-acetylene. For such processes, the partial pressure detector can be calibrated at the start of the process for one of the two gas types, as described above with regard to $N_2$ for lyophilization processes. The other of the two gas types can be the species for which a partial pressure is measured.

Partial pressure detectors, such as detectors 400 and 700, advantageously provide operators of lyophilization systems (or other gas systems, such as binary gas systems) with the convenience of a straightforward measurement of an actual amount of water (or other species) in the system. Currently, operators of constant-pressure lyophilization systems independently read the total pressure outputs of both a capacitance manometer and a Pirani gauge and calculate a ratio of the two outputs to determine whether there is a sufficiently small amount of water remaining in the system to end a process. Alternatively, operators integrate such sensors to a centralized software program that is configured to display the total pressure outputs and/or calculate a ratio of the total pressure readings of the two sensors. Operators may instead predetermine an acceptable difference in total pressure between the Pirani gauge and capacitance manometer. However, in all such processes, the operators must predetermine an acceptable value for indicating the end of a drying process, account for differences in accuracy between the Pirani gauge and the more-accurate capacitance manometer, which are not calibrated to one another, and rely on total pressures reported by the two gauges to infer an acceptable amount of water content for a process end point.

In contrast, partial pressure detectors, such as detectors 400 and 700, can output a direct measurement of an amount of water in the system, for example, either a weighted partial pressure or an actual partial pressure of water, thereby enabling operators to straightforwardly determine a process endpoint based on an acceptable amount of water. Furthermore, partial pressure detectors can provide for such output from a single device, which conveniently alleviates or eliminates the need to separately install and calibrate several independent sensors and/or setup a separate software application to consolidate outputs of the several sensors.

Further still, partial pressure detectors, such as detectors 400 and 700, can advantageously provide for higher sensitivity with regard to detecting changes in water content. By having an output with a resolution scaled to an expected range of partial pressures, as opposed to total pressures, significantly improved step resolution can be achieved with regard to those measurements most relevant to process endpoints. With increased step resolution and more precise measurements of water content, more consistent end point detection can be achieved for both primary and secondary drying processes.

The inclusion of a trigger for zeroing output of the partial pressure detector advantageously provides for a straightforward calibration procedure of a thermal conductivity gauge to a more accurate species-independent sensor. In current lyophilization systems, the Pirani sensor and the capacitance manometer are not calibrated against one other. Rather, the Pirani sensor is independently calibrated against a number of known pressures, and as Pirani sensors are prone to drift, operators are often subject to monitoring Pirani sensor accuracies and routinely performing complicated calibration procedures. In contrast, partial pressure detectors, such as detectors 400 and 700, can be calibrated by a relatively easy procedure. The zeroing of the output of the thermal conductivity gauge, such as a Pirani gauge, to a more accurate species-independent sensor can advantageously account for intrinsic differences in accuracy between the two sensors as well as for any drift that may occur over time. As the calibration process can be repeated before each lyophilization process with minimal effort, more consistent end point detection can be achieved.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:
1. A partial pressure detector, comprising:
a thermal conductivity sensor configured to sense a pressure of a mixture of gases within a vacuum chamber;
an input configured to receive a total pressure reading from a species-independent pressure sensor of the mixture of gases in the vacuum chamber; and
a controller configured to provide an output representing a partial pressure of a species of gas in the vacuum chamber according to a function as follows:

$$PP_S = \frac{TP_{PG} - TP}{x}$$

where $TP_{PG}$ is the pressure as sensed by the thermal conductivity sensor, TP is the total pressure as received from the species-independent pressure sensor, x is a species-dependent factor, and PPs is the partial pressure of the species, the controller having a resolution scaled to a range of expected partial pressures of the species such that an output signal range of the controller is assigned to correspond to the range of expected partial pressures.

2. The partial pressure detector of claim 1, wherein the species is water and x is about 0.4.

3. The partial pressure detector of claim 1, wherein the controller is further configured to provide a second output, the second output representing a total pressure of the mixture of gases within the vacuum chamber as sensed by the thermal conductivity sensor.

4. The partial pressure detector of claim 1, wherein the thermal conductivity sensor is a Pirani sensor.

5. The partial pressure detector of claim 1, wherein the species-independent sensor is a capacitance manometer.

6. The partial pressure detector of claim 1, further comprising an input port configured to connect to an output of the species-independent pressure sensor.

7. The partial pressure detector of claim 1, further comprising the species-independent pressure sensor.

8. The partial pressure detector of claim 1, further comprising a trigger configured to zero the output of the controller.

9. The partial pressure detector of claim 1, wherein the controller is further configured to adaptively average the output.

10. The partial pressure detector of claim 1, wherein the range of expected partial pressures of the species is of a solvent in a primary or secondary drying process for lyophilization.

11. The partial pressure detector of claim 1, wherein the range of expected partial pressures of the species is of about 0 to about 0.01 Torr.

12. A partial pressure detector, comprising:
a housing;
a thermal conductivity sensor at least partially contained within the housing and configured to sense a thermal response of a sensor wire to a mixture of gases within a vacuum chamber; and
a controller, contained within the housing, configured to:
determine a pressure of the mixture of gases within the vacuum chamber based on the sensed thermal response of the thermal conductivity sensor,
receive a total pressure reading from a species-independent pressure sensor of the mixture of gases in the vacuum chamber, and
provide an output representing a partial pressure of a species of gas in the vacuum chamber according to a function as follows:

$$PP_S = \frac{TP_{PG} - TP}{x}$$

where $TP_{PG}$ is the determined pressure based on the sensed thermal response of the thermal conductivity sensor, TP is the total pressure as received from the species-independent pressure sensor, x is a species-dependent factor, and PPs is the partial pressure of the species, the controller having a resolution scaled to a range of expected partial pressures of the species such that an output signal range of the controller is assigned to correspond to the range of expected partial pressures.

13. The partial pressure detector of claim 12, wherein the species is water and x is about 0.4.

14. The partial pressure detector of claim 12, wherein the controller is further configured to provide a second output, the second output representing a total pressure of the mixture of gases within the vacuum chamber as determined based on the sensed thermal response of the thermal conductivity sensor.

15. The partial pressure detector of claim 12, wherein the thermal conductivity sensor is a Pirani sensor.

16. The partial pressure detector of claim 12, wherein the species-independent pressure sensor is a capacitance manometer.

17. The partial pressure detector of claim 12, further comprising an input port configured to connect to an output of the species-independent pressure sensor.

18. The partial pressure detector of claim 12, further comprising the species-independent pressure sensor.

19. The partial pressure detector of claim 18, wherein the species-independent pressure sensor is contained within the housing.

20. The partial pressure detector of claim 12, further comprising a trigger configured to zero the output of the controller.

21. The partial pressure detector of claim 12, wherein the controller is further configured to adaptively average the output.

22. A method of detecting a partial pressure of a gas species, comprising:
with a thermal conductivity sensor, sensing a pressure of a mixture of gases within a vacuum chamber;
with a species-independent pressure sensor, sensing a total pressure of the mixture of gases within the vacuum chamber; and
providing an output representing a partial pressure of a species of gas in the vacuum chamber according to a function as follows:

$$PP_S = \frac{TP_{PG} - TP}{x}$$

where $TP_{PG}$ is the pressure as sensed by the thermal conductivity sensor, TP is the total pressure as sensed by the species-independent pressure sensor, x is a species-dependent factor, and PPs is the partial pressure of the species, the output provided by a controller having a resolution scaled to a range of expected partial pressures of the species such that an output signal range of the controller is assigned to correspond to the range of expected partial pressures.

23. The method of claim 22, wherein the species is water and x is about 0.4.

24. The method of claim 22, further comprising providing a second output, the second output representing a total pressure of the mixture of gases within the vacuum chamber as sensed by the thermal conductivity sensor.

25. The method of claim 22, wherein the species is a solvent of a sample undergoing lyophilization in the vacuum chamber.

26. The method of claim 22, wherein the mixture of gases is binary.

27. The method of claim 22, wherein the thermal conductivity sensor is a Pirani sensor.

28. The method of claim 22, wherein the species-independent sensor is a capacitance manometer.

29. The method of claim 22, further comprising calibrating the controller to the species-independent pressure sensor.

30. The method of claim 29, further comprising zeroing an output of the controller.

31. The method of claim 22, further comprising adaptively averaging the output.

32. The method of claim 22, wherein the range of expected partial pressures of the species is of a solvent in a primary or secondary drying process for lyophilization.

33. The method of claim 22, wherein the range of expected partial pressures of the species is of about 0 to about 0.01 Torr.

34. A partial pressure detector, comprising:
a species-dependent sensor configured to sense a pressure of a mixture of gases within a vacuum chamber;
an input configured to receive a total pressure reading from a species-independent pressure sensor of the mixture of gases in the vacuum chamber; and
a controller configured to provide an output representing a partial pressure of a species of gas in the vacuum chamber according to a function as follows:

$$PP_S = \frac{TP_{PG} - TP}{x}$$

where $TP_{PG}$ is the pressure as sensed by the species-dependent sensor, TP is the total pressure as received from the species-independent pressure sensor, x is a species-dependent factor, and PPs is the partial pressure of the species, the controller having a resolution scaled to a range of expected partial pressures of the species such that an output signal range of the controller is assigned to correspond to the range of expected partial pressures.

* * * * *